United States Patent [19]

Young

[11] 4,225,504
[45] Sep. 30, 1980

[54] MONOMERIC N-METHYLENEAMINOACETONITRILE

[75] Inventor: E. Richard Young, Nashua, N.H.

[73] Assignee: W. R. Grace & Co., New York, N.Y.

[21] Appl. No.: 954,608

[22] Filed: Oct. 25, 1978

[51] Int. Cl.² .................. C07C 121/42; C07C 120/00
[52] U.S. Cl. .................... 260/465.5 A; 260/465.5 R
[58] Field of Search ............... 260/465.5 A, 465.5 R

[56] References Cited

U.S. PATENT DOCUMENTS

| | | | |
|---|---|---|---|
| 2,085,679 | 6/1937 | Gluud et al. | 260/465.5 R |
| 2,405,966 | 8/1946 | Loder | 260/465.5 A |
| 2,720,540 | 10/1955 | Caverly | 260/534 |
| 2,823,222 | 2/1958 | Sexton et al. | 260/465.5 R |
| 3,009,954 | 11/1961 | Leake et al. | 260/534 |
| 3,096,362 | 7/1963 | Sexton | 260/465.5 A |
| 3,167,581 | 1/1965 | Saunders et al. | 260/465.5 A |
| 3,167,582 | 1/1965 | Saunders et al. | 260/465.5 A |
| 3,256,314 | 6/1966 | Dovell et al. | 260/465.5 A |
| 3,499,920 | 3/1970 | Daniels | 260/465.5 R |
| 3,875,221 | 4/1975 | Mihara et al. | 562/554 X |
| 4,022,815 | 5/1977 | Schlecht et al. | 260/465.5 A |
| 4,113,764 | 9/1978 | Distler et al. | 260/465.5 A |

OTHER PUBLICATIONS

Adams, et al., *Organic Synthesis*, Coll. vol. 1 (1932), pp. 347-348.
Jay et al., *Ber.*, 27, pp. 59-62 (1894).
Klages, Methyleneaminoacetonitride, *J. Prakt. Chem.*, (2), 65, 192 (1902), translation thereof.
Delphine, *Academie des Sciences*, pp. 60-63 (1963), translations thereof.
Rinehard, *J.A.C.S.*, 48 (1926), pp. 2794-2798.

*Primary Examiner*—Joseph P. Brust
*Attorney, Agent, or Firm*—Donald G. Marion

[57] ABSTRACT

The novel monomeric compound N-methyleneaminoacetonitrile is produced by reacting glycinonitrile with formaldehyde in the absence of ammonia. The process is conveniently carried out by forming aqueous glycinonitrile in situ using known methods, removing any excess ammonia from the reaction medium and then introducing at least an equimolar amount of formaldehdye. The reaction is allowed to proceed substantially to completion. The novel product has a higher melting point than the previously reported trimer.

8 Claims, 2 Drawing Figures

MONOMERIC N-METHYLENEAMINOACETONITRILE

BACKGROUND OF THE INVENTION

This invention relates to the preparation of nitriles and more in particular it relates to the production of monomeric N-methyleneaminoacetonitrile.

The previously known N-methyleneaminoacetonitrile trimer has been used as an intermediate for many reactions where glycinonitrile is useful, such as the production of glycine or the manufacture of imino diacetic acid. It has the advantage that it is more stable than glycinonitrile and thus has a better shelf life. It is also less soluble in water thus facilitating recovery from the reaction medium. It has been found that the monomeric compound of this invention has similar utility and advantages to the trimer and is simpler to produce.

N-methyleneaminoacetonitrile trimer, also called N-methylene glycinonitrile (trimer) has previously been prepared by several different routes. A classical procedure for the preparation of the trimer is that described by Klages in *J. prakt. Chem.* (2), 65, 192 (1902). At the time, Klages believed the product to be the dimer. There is further confusion in the literature as the trimer product has often been named as the monomer. This particular preparative method is not attractive commercially because it involves the use of an expensive intermediate, glycinonitrile hydrochloride.

N-methyleneaminoacetonitrile trimer has also been prepared by the reaction of formaldehyde, an ammonium halide and an alkali metal cyanide in the presence of acid as described by Jay and Curtius, *Ber.* 27, 59 (1894) and later, by Adams and Langley, *Organic Synthesis,* Coll. Vol. I, 347 (1932). Recently, an improvement upon this basic process was described in U.S. Pat. No. 2,823,222.

U.S. Pat. No. 3,167,581, issued Jan. 26, 1965 suggests a continuous preparation of trimeric N-methyleneaminoacetonitrile directly from formaldehyde, hydrogen cyanide and ammonia. See also U.S. Pat. Nos. 3,256,314 and 3,096,362 for other prior art processes.

However, the above processes produce products which are the trimer of N-methyleneaminoacetonitrile and not the monomer. The trimeric products have a melting point of about 129° C. and have the characteristic infrared spectrum shown in FIG. 2. In contradistinction, the process of this invention is directed to the production of the hitherto unknown monomeric form. This unique product has a melting point of about 167°–170° C. and the infrared spectrum shown in FIG. 1.

SUMMARY OF THE INVENTION

N-methyleneaminoacetonitrile is produced in monomeric form by reacting glycinonitrile with formaldehyde, in the absence of ammonia. The process can be carried out by producing glycinonitrile in situ, removing unreacted ammonia from the reaction medium, and then further reacting it with formaldehyde. The process may be carried out at any convenient temperature range, but a temperature of about 0° C. to about 50° C. has been found to be useful. The product is insoluble in the aqueous reaction medium and is easily recovered by filtration.

DETAILED DESCRIPTION OF THE PREFERRED EMBODIMENTS

Figure 1:
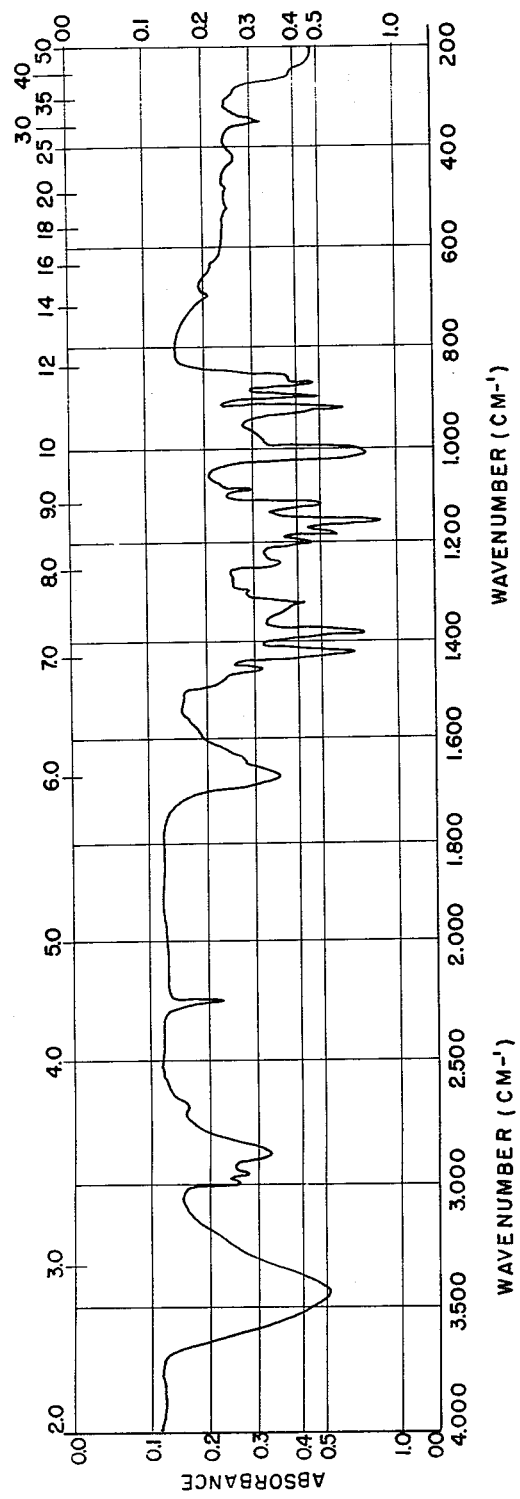
FIG. 1 is the infrared spectrum of the product of this invention.

N-methyleneaminoacetonitrile is the product of the reaction of equimolar amounts of formaldehyde and glycinonitrile in accordance with the following equation:

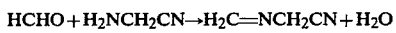

$$HCHO + H_2NCH_2CN \rightarrow H_2C=NCH_2CN + H_2O$$

While the equation appears to describe a relatively simple reaction, it is deceptive as generally it does not proceed as described but yields the trimeric form of N-methyleneaminoacetonitrile having the formula:

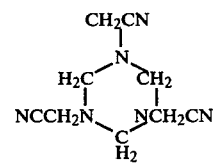

It has now been found that the monomeric form of this compound may be prepared directly from glycinonitrile and formaldehyde by carrying out the reaction in the absence of ammonia. If ammonia is permitted to be present in the reaction mixture, then only the trimeric form will be produced. It is not known why this should be the case, but it may be speculated that the presence of ammonia allows the production of an intermediate amine form which readily yields the trimer. As both glycinonitrile and formaldehyde are quite soluble in water, the reaction in conveniently carried out in an aqueous medium. Inasmuch as the product is only sparingly soluble in water it crystallizes from the aqueous reaction mixture during the course of the reaction and is easily recovered by filtration.

The concentration of the glycinonitrile in the starting aqueous solution is not critical but should be high enough so that inconveniently large volumes of water are not used. Generally, concentrations in the range of about 20% to about 75% are useful, and it is most convenient to use any reasonable commercial concentration, such as from about 20% to about 40%.

While the glycinonitrile solution may be prepared directly by admixing it with water, glycinonitrile is an unstable substance and preferably is prepared in situ immediately prior to its further reaction in accordance with this invention.

Glycinonitrile has been prepared by a number of prior art processes. See e.g., U.S. Pat. Nos. 2,085,679, 3,167,582, and 3,875,221. Any convenient process may be utilized. For example, the following procedure may be used:

Charge 219.8 g (3.75 moles) of 29% aqueous ammonia to a stirred 450 ml. pressure reactor. Preheat the reactor to 80° C. and pump 71.3 g (0.75 mole) of 60% glycolonitrile into the reactor over a period of five minutes. Pump in 50 ml of water to wash the glycolonitrile solution into the reactor. After allowing the reaction to proceed for six minutes, cool the reactor, and recover the product. The reaction generally proceeds 95–98% to completion under these conditions.

The glycinonitrile must be free of ammonia. Inasmuch as the above process utilizes a large excess of ammonia, it is necessary that it be removed. While any convenient method may be utilized, it is simplest to merely evaporate the ammonia along with a portion of the water. This is generally done at reduced pressures so the temperature may be kept low to reduce the risk of decomposition of the glycinonitrile. The temperature is preferably kept below about 40° C. Alternatively the ammonia could be neutralized with acid, removed using an ion exchange column, etc. However, these other methods are generally expensive and thus not commercially viable.

The temperature of the reaction medium is then adjusted to the desired temperature range and maintained in that range for the duration of the reaction. A temperature in the range of about 0° C. to about 50° C. has been found to be convenient. As the reaction is exothermic a means of cooling the reaction vessel is generally used, particularly at lower temperatures. Adding the formaldehyde slowly also helps keep the temperature down.

Acetic acid may be optionally added at this time. Generally about ½ mole of acetic acid per mole of glycinonitrile may be used, but any amount in the range of 0 to about 2 moles of acetic acid per mole of glycinonitrile may be used.

The formaldehyde is then introduced slowly (dropwise) into the reaction vessel. It is important that the formaldehyde be added slowly so as to control the rate of reaction and thus the temperature.

The concentration of the formaldehyde is not critical and generally the commercial 40% product is suitable. The total formaldehyde should be equimolar with the glycinonitrile to produce the highest theoretical yield. In practice, a slight excess (about 5%) of formaldehyde is used to ensure that the reaction goes to completion.

After the addition of the formaldehyde, the reaction mixture is maintained under reactive conditions for an additional period of time to ensure completeness of reaction. Times of one-half hour to one hour are generally sufficient.

The product is then filtered, washed and dried. In order to characterize the resulting product, the melting point was determined by the capillary method.

The melting point was determined to be 167° C.–170° C. When the familiar trimer was tested using the identical procedure, its melting point was 126° C.–131° C.

The infrared spectrums of both the product of this invention and the prior art trimer were then determined by forming a KBr pellet containing 1 part of compound per 300 parts KBr. The spectrum was then determined in the usual way using a Perkin-Elmer 457 Infrared Spectrograph.

Figure 2:
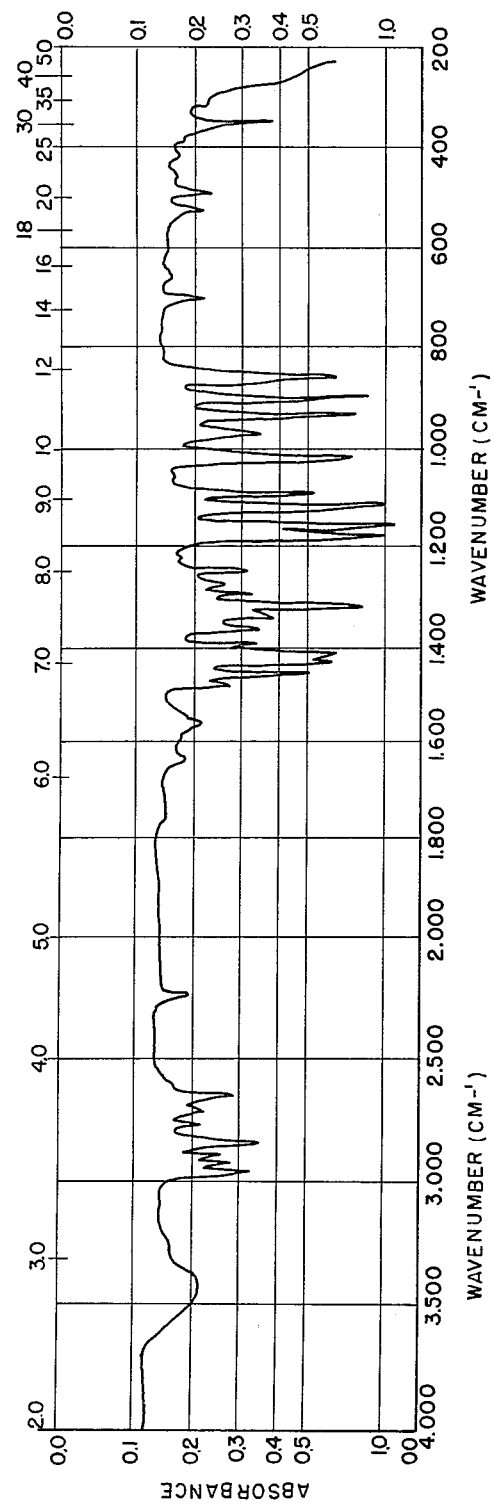
FIG. 2 is the infrared spectrum of the product of the Comparative Example (prior art).

The product of this invention yielded the spectrum of FIG. 1 while the prior art product yielded that of FIG. 2. A number of substantial differences appear between the two and in particular the spectrum of FIG. 1 exhibits a strong band at 1670 cm$^{-1}$, characteristic of the $>C=N-$ bond while the spectrum of FIG. 2 does not. In order to provide a better understanding of this invention the following non-limiting examples are provided:

EXAMPLE 1

An aqueous glycinonitrile solution (0.75 mole) was prepared which was about 12% glycinonitrile and 15% ammonia. Immediately after cooling the reaction, this solution was transferred to a single neck flask. The contents were evaporated to 110 g at 40° C. under reduced pressure. The resulting solution contained approximately 38% glycinonitrile and no free ammonia.

The solution was transferred to a three neck flask and cooled to 0°–5° C. in an ice bath. While maintaining this temperature, 21.5 ml (0.375 moles) of glacial acetic acid were introduced into the flask over a period of about one hour. A solution containing 52.1 g (0.765 moles) of 44.1% formaldehyde (which had been previously clarified by filtration) and 21 ml of water was introduced into the flask dropwise over a period of two hours 46 minutes. A white solid began to form about two minutes after the addition was begun. The temperature was maintained with stirring for an additional one hour period, and a resulting product was filtered, washed with two 10 ml portions of water and dried in a vacuum desiccator. The product weighed 44.4 g. and had a melting point of 167° to 170° C. Its infrared spectrum is shown as FIG. 1. Analysis for nitrogen by the Kjeldahl method gave 41.4% total nitrogen and 20.4% saponifiable nitrogen. The theoretical values for this compound are 41.2% total nitrogen and 20.6% saponifiable nitrogen.

EXAMPLE 2

Four batches of glycinonitrile were prepared in a similar manner to the procedure of Example 1. They were combined prior to the evaporation step. The resulting solution was divided into three portions of 147.7 g., which were stored in a frozen state.

The first portion was heated to 40° C. Then a solution containing 71.7 g. (1.05 mole) of 44.1% formaldehyde and 15 ml water was added dropwise over a period of 43 min. The temperature remained at about 40° C. until crystallization began (about halfway through the addition). The solution then had to be cooled in an ice bath to prevent the temperature from rising due to heat of crystallization of the product. Upon completion of the addition, the mixture was stirred for about ½ hour while heating to maintain the 40° C. temperature.

The mixture was then cooled to 5° C. and filtered. The product was washed with two 10 ml portions of water and then dried in a vacuum desiccator. It was then further dried at 50° C. in an oven. The yield was 55.7 g. of a tan product having a melting point of 151°–154° C. and the infrared spectrum of FIG. 1.

EXAMPLE 3

Example 2 was repeated using a second portion of glycinonitrile except that the reaction was carried out at 30° C. The product (yield 58.5 g.) was tan, had a melting point of 150°–155° C. and had the infrared spectrum of FIG. 1.

EXAMPLE 4

Example 2 was repeated using the third portion of glycinonitrile except that the reaction was carried out at 50° C. The tan product (yield 55.3 g.) had a melting point of 154°–158° C. and had the infrared spectrum of FIG. 1.

The products of Examples 2, 3, and 4 were combined and analyzed for nitrogen by Kjeldahl distillation. The composite had 40.2% total N and 21.0% saponifiable N.

COMPARATIVE EXAMPLE

This example follows the teaching of *Organic Synthesis*, Coll. Vol. 1, p. 356 for the production of methyleneaminoacetonitrile.

265.6 g. (3.78 moles) of 42.7% formaldehyde and 98.0 g. (1.96 moles) of 98% ammonium chloride were charged into a 1 liter flask. Chunks of dry ice were added to cool the mixture to less than about 5° C. 76 ml (1.33 moles) of glacial acetic acid was rapidly added. A solution of 107.0 g. (2.0 moles) of sodium cyanide in 170 ml of water was added dropwise over a period of ½ hour. The temperature was maintained at less than about 15° C. by the addition of dry ice. Halfway through the addition a slurry of product began to form. The reaction mixture was allowed to stand for 15 min. after the completion of the addition. The product was then filtered, reslurried in 300 ml of water, filtered again and washed with two 50 ml portions of water. 74.2 g. of a white, crystalline product were obtained. The melting point was 126°–131° C. and the product had the infrared spectrum of FIG. 2.

We claim:

1. A process for the production of N-Methyleneaminoacetonitrile the steps consisting of:
   (a) forming an aqueous solution of glycinonitrile which is free of ammonia;
   (b) slowly introducing sufficient aqueous formaldehyde into said solution to produce at least an equimolar quantity with said glycinonitrile;
   (c) maintaining the temperature of said aqueous mixture in the range of from about 0° C. to about 50° C.; and
   (d) allowing said formaldehyde to react with said glycinonitrile until the product is formed.

2. A process in accordance with claim 1, wherein the product is recovered from the reaction mixture.

3. A process in accordance with claim 1, wherein the concentration of glycinonitrile is in the range of from about 20 percent to about 75 percent, based on total weight of aqueous solution.

4. A process in accordance with claim 1, wherein said reaction mixture further includes up to about 2 moles of acetic acid per mole of glycinonitrile.

5. A process in accordance with claim 1, wherein said glycinonitrile is produced in situ.

6. A compound having the empirical formula $C_3H_4N_2$, a white color, a melting point in the range of about 167° C. to about 170° C. and the infrared spectrum of FIG. 1 and being sparingly soluble in water said compound being a monomeric compound having the formula $H_2C=N-CH_2-CN$.

7. The product of the process of claim 1.

8. The product of the process of claim 4.